US010310778B2

(12) United States Patent
Boccanfuso et al.

(10) Patent No.: US 10,310,778 B2
(45) Date of Patent: Jun. 4, 2019

(54) SYSTEM AND METHODS FOR PRINTING MEDICAL IMAGES FROM AN INTERNET BROWSER

(71) Applicant: AGFA HEALTHCARE N.V., Mortsel OT (BE)

(72) Inventors: Giovan Giuseppe Boccanfuso, Heidelberg (CA); Robert A. Lowe, Waterloo (CA)

(73) Assignee: AGFA HEALTHCARE N.V., Mortsel (BE)

( * ) Notice: Subject to any disclaimer, the term of this patent is extended or adjusted under 35 U.S.C. 154(b) by 203 days.

(21) Appl. No.: 15/264,731

(22) Filed: Sep. 14, 2016

(65) Prior Publication Data

US 2018/0074759 A1 Mar. 15, 2018

(51) Int. Cl.
*G06F 3/00* (2006.01)
*G06F 3/12* (2006.01)
(Continued)

(52) U.S. Cl.
CPC ........... *G06F 3/1208* (2013.01); *G06F 3/125* (2013.01); *G06F 3/1225* (2013.01);
(Continued)

(58) Field of Classification Search
CPC ..... G16H 50/50; G06F 3/1225; G06F 3/1206; G06F 17/211; G06F 17/2247;
(Continued)

(56) References Cited

U.S. PATENT DOCUMENTS 6,574,629 B1 * 6/2003 Cooke, Jr. ......... G06F 17/30017
7,496,242 B2   2/2009 Hunt
(Continued)

FOREIGN PATENT DOCUMENTS

CA    2216123 A1    3/1998
WO    02/084517 A1  10/2002

OTHER PUBLICATIONS

"Set Internet Explorer to open links in a new window automatically," Jun. 1, 2004, <https://www.techrepublic.com/article/set-internet-explorer-to-open-links-in-a-new-windowautomatically/>, pp. 1-8.*

(Continued)

*Primary Examiner* — Kyle R Stork
(74) *Attorney, Agent, or Firm* — Lewis Rice LLC

(57) ABSTRACT

A system and method for printing medical images is provided. The system includes a client device and a server in data communication with the client device. The client device includes a communication subsystem for receiving medical images from the server; a user interface device for displaying the medical images in an Internet browser and receiving a request to print at least one selected medical image; and a processor coupled to a memory for storing a plurality of instructions. The processor can be configured for generating a base model that includes at least one page required to print the at least one selected medical image, generating a printable model by, for each of the at least one selected medical image, rendering that selected image to an image element of a page of the base model; and transferring the printable model to a model printable by the Internet browser.

18 Claims, 12 Drawing Sheets

(51) Int. Cl.
*G16H 50/50* (2018.01)
*G06F 17/21* (2006.01)
*G06F 17/22* (2006.01)
*G06F 19/00* (2018.01)
*G06T 3/00* (2006.01)
*G06T 3/40* (2006.01)
*G06T 11/60* (2006.01)
*G06F 3/0482* (2013.01)

(52) U.S. Cl.
CPC .......... *G06F 3/1247* (2013.01); *G06F 17/211* (2013.01); *G06F 17/2247* (2013.01); *G06F 19/321* (2013.01); *G06T 3/0056* (2013.01); *G06T 3/40* (2013.01); *G06T 11/60* (2013.01); *G16H 50/50* (2018.01); *G06F 3/0482* (2013.01); *G06F 3/1206* (2013.01); *G06F 2206/1512* (2013.01); *G06T 2200/24* (2013.01); *G06T 2210/41* (2013.01)

(58) Field of Classification Search
CPC .. G06F 19/321; G06F 19/3437; G06F 3/1208; G06F 31/1247; G06F 3/125; G06F 3/0482; G06F 2206/1512; G06T 3/0056; G06T 3/40; G06T 11/60; G06T 2210/41; G06T 2200/24
See application file for complete search history.

(56) References Cited

U.S. PATENT DOCUMENTS

| | | | | |
|---|---|---|---|---|
| 8,418,068 | B1* | 4/2013 | Backus | H04N 1/00167 345/619 |
| 8,489,410 | B2* | 7/2013 | Rothpearl | G06F 17/30265 705/2 |
| 8,520,978 | B2 | 8/2013 | Jakobovits | |
| 8,869,023 | B2 | 10/2014 | Berkner et al. | |
| 2003/0028401 | A1 | 2/2003 | Kaufman et al. | |
| 2003/0046268 | A1 | 3/2003 | Hirabayashi | |
| 2004/0019628 | A1 | 1/2004 | Puri et al. | |
| 2004/0054983 | A1* | 3/2004 | Noguchi | H04N 1/00132 717/100 |
| 2006/0259855 | A1* | 11/2006 | Crucs | G16H 40/63 715/210 |
| 2007/0157193 | A1 | 7/2007 | Lowe et al. | |
| 2009/0207447 | A1 | 8/2009 | Keane et al. | |
| 2010/0325568 | A1* | 12/2010 | Pedersen | G06F 17/30994 715/765 |
| 2013/0107311 | A1 | 5/2013 | Eng et al. | |
| 2014/0245130 | A1* | 8/2014 | Ferreira | G06F 3/1203 715/234 |
| 2015/0030218 | A1 | 1/2015 | Boccanfuso et al. | |
| 2015/0304171 | A1* | 10/2015 | Kim | H04L 67/125 715/733 |
| 2016/0274852 | A1* | 9/2016 | Katabami | G06F 3/1286 |

OTHER PUBLICATIONS

"Configure browser to use the Adobe PDF plug-in," Jan. 12, 2016, <https://web.archive.org/web/20160112232720/https://helpx.adobe.com/acrobat/kb/pdf-browser-plugin-configuration.html>, pp. 1-5. (Year: 2016).*
International Search Report and Written Opinion dated Dec. 11, 2017 in corresponding International Patent Application No. PCT/CA2017/051081.
Liu, et al., "iMAGE cloud: medical image processing as a service for regional healthcare in a hybrid cloud environment", Environ Health Prey Med, 2016, 21(6): 563-571.
Varma, "Managing DICOM images: Tips and tricks for the radiologist", Indian Journal of Radiology and Imaging, 2012, 22(1): 4-13.
Graham, et al., "DICOM demystified: A review of digital file formats and their use in radiological practice", Clinical Radiology, 2005, 60(11): 1133-1140.

* cited by examiner

SYSTEM AND METHODS FOR PRINTING MEDICAL IMAGES FROM AN INTERNET BROWSER

FIELD

Exemplary embodiments described herein relate to systems and methods in the medical field. More specifically, they relate to a system and method for printing medical images of medical studies from a web application.

BACKGROUND

Medical studies are conducted to collect evidence about a patient's condition in order to formulate a clinical diagnosis. The evidence collected is compiled in a report, herein referred to as the medical study. The information collected can include medical images.

Various users, particularly clinicians, physicians, and general practitioners, often refer to the medical studies. Furthermore, nurses, physician assistants, and receptionists, may also require access to medical studies. Medical studies can be distributed to users through a web application using an Internet browser operating at a computing device.

In addition to viewing medical studies in an Internet browser from a computing device, users may wish to print the medical study. The printouts can be used to access the medical study when a computer device, particularly web access, is not available. The printouts can also be provided to patients for their own records, subsequent medical appointments, and referrals.

Internet browsers (e.g., Apple Safari®, Google Chrome™, Microsoft Internet Explorer®, Microsoft Edge™, Mozilla Firefox®, etc.) have a printing function to print web pages being viewed. However, printouts generated from the Internet browser printing function are typically "What You See Is What You Get" (WYSIWYG). That is, the Internet browser printing function prints the entire web page being viewed, including elements that are not of interest such as, but not limited to, advertisements, web application menus, and tool icons.

In addition, the printing function of an Internet browser does not generally provide for intelligent paging, which ensures that any single medical images is not printed across multiple pages. That is, the printouts using the Internet browser printing function may include a medical image that is split across more than one page. Furthermore, the printing function of an Internet browser may not provide for selective printing of medical images and information from the totality of medical images and information available in the medical study.

SUMMARY

In accordance with an embodiment, there is provided a computer-implemented method of printing medical images. The method can involve displaying, in an Internet browser at a client device, one or more medical images received from a server; receiving, at the client device, a request to print at least one selected medical image of the one or more medical images; generating, at the client device, a base model comprising at least one page required to print the at least one selected medical image; generating, at the client device, a printable model; and transferring the printable model to a model printable by the Internet browser. Each page of the base model has identical image elements as any other page of the base model. To generate the printable model, each of the at least one selected medical image can be rendered to an image element of a page of the base model.

In some embodiments, the method further involves providing a medical images printing application at the client device. The medical images printing application can include a single image rendering object and the rendering each of the at least one selected medical image to an image element of a page of the base model can involve reusing the single image rendering object to render each of the at least one selected medical image to an image element of the base model.

In some embodiments, the at least one selected medical image can include an ordered set of one or more selected medical images. The ordered set of one or more selected medical images can include a first selected medical image and one or more subsequent selected medical images. Each of the subsequent selected medical images can have a corresponding previous selected medical image. The reusing the single image rendering object to render each of the at least one selected medical image to an image element of the base model can involve, for each subsequent selected medical image, rendering the subsequent selected medical image after the corresponding previous selected medical image has been rendered.

In some embodiments, the method further involves upon receiving the request to print the at least one selected medical image of the one or more medical images, initializing a progress meter; and for each of the at least one selected medical image, upon rendering that selected image to an image element of the base model, updating the progress meter to indicate an amount of selected medical images that have been rendered.

In some embodiments, the model printable by the Internet browser involves a document object model of an Internet browser frame.

In some embodiments, the method further involves loading a new Internet browser frame at the client device; and the Internet browser frame to which the printable model is transferred to is the new Internet browser frame.

In some embodiments, the method further involves, after transferring the printable model to a model printable by the Internet browser: providing notification, at the client device, that the request is ready for printing using the Internet browser; receiving, at the client device, a confirmation to print the model printable by the Internet browser; and sending the model printable by the Internet browser to a printer at the client device.

In some embodiments, the generating a base model involves retrieving a default page model to print at least one selected medical image of the one or more medical images, creating a single page model based on the request, and creating a base model based on the single page model and the request. The default page model can include a printable area element. The single page model can include the default page model and at least one of an image element, a header section element, and a footer section element. Each of the at least one of the image element, the header section element, and the footer section element can include area allocated to the printable area element.

In some embodiments, the default page model includes a printable area element and margin elements. The margin elements can include a top margin element located along a top edge of the default page model, a bottom margin element located along a bottom edge of the default page model, a left margin element located along a left edge of the default page model, and a right margin element located along a right edge of the default page mode. The printable area element can include area on the default page model not allocated to at least one of the margin elements.

In some embodiments, the creating a single page model based on the request involves determining an image area based on the printable area element of the default page model and the request. The image area can include an image area width and an image area height.

In some embodiments, the determining an image area based on the printable area element of the default page model and the request involves determining the image area width based on a width of the printable area element of the default page model.

In some embodiments, the determining an image area based on the printable area element of the default page model and the request involves determining the image area height by creating a test model; rendering the test model to a document object model of the Internet browser; measuring, from the document object model having the test model, a shortest distance between the header element and the footer element; and determining the image area height based on the shortest distance between the header element and the footer element. The test model can include the default page model, a header element and a footer element. The header element can include area allocated to the printable area element and located along a top edge of the printable area element. The header element can have an associated height based on the request. The footer element can include area allocated to the printable area element and located along a bottom edge of the printable area element. The footer element can have an associated height based on the request.

In some embodiments, the request includes a selected image layout, which includes a number of image rows per page and a number of image columns per page. The creating a single page model based on the request can involve determining an image element height based on the image area height divided by the number of image rows per page; determining an image element width based on the image area width divided by the number of image columns per page; and adding at least one image element to the single page model based on the selected image layout. The at least one image element can include area allocated to the image area. Each of the image elements can have the image element height and the image element weight.

In some embodiments, the creating a base model based on the single page model and the request involves determining a number of pages required to print the at least one selected medical image based on the selected image layout; and duplicating the single page model for the number of pages required to print the at least one selected medical image.

In accordance with another embodiment, there is provided a system for printing medical images. The system can include a server in data communication with a client device, and the client device. The client device can include a communication subsystem for receiving one or more medical images from the server; a user interface device for displaying the one or more medical images in an Internet browser and receiving a request to print at least one selected medical image of the one or more medical images; a memory for storing a plurality of instructions; and a processor coupled to the memory. The processor can be configured for generating a base model, generating a printable model, and transferring the printable model to a model printable by the Internet browser. The base model can include at least one page required to print the at least one selected medical image. Each page of the base model can have identical image elements as any other page of the base model. To generate a printable model, each of the at least one selected medical image can be rendered to an image element of a page of the base model.

In some embodiments, the at least one selected medical image can include an ordered set of one or more selected medical images. The ordered set of one or more selected medical images can include a first selected medical image and one or more subsequent selected medical images. Each of the subsequent selected medical images can have a corresponding previous selected medical image. The rendering each of the at least one selected medical image to an image element of a page of the base model can involve, for each subsequent selected medical image, rendering the subsequent selected medical image after the corresponding previous selected medical image has been rendered.

Further aspects and advantages of the embodiments described herein will appear from the following description taken together with the accompanying drawings.

BRIEF DESCRIPTION OF THE DRAWINGS

For a better understanding of the embodiments described herein and to show more clearly how they may be carried into effect, reference will now be made, by way of example only, to the accompanying drawings which show at least one exemplary embodiment, and in which.

Figure 1:
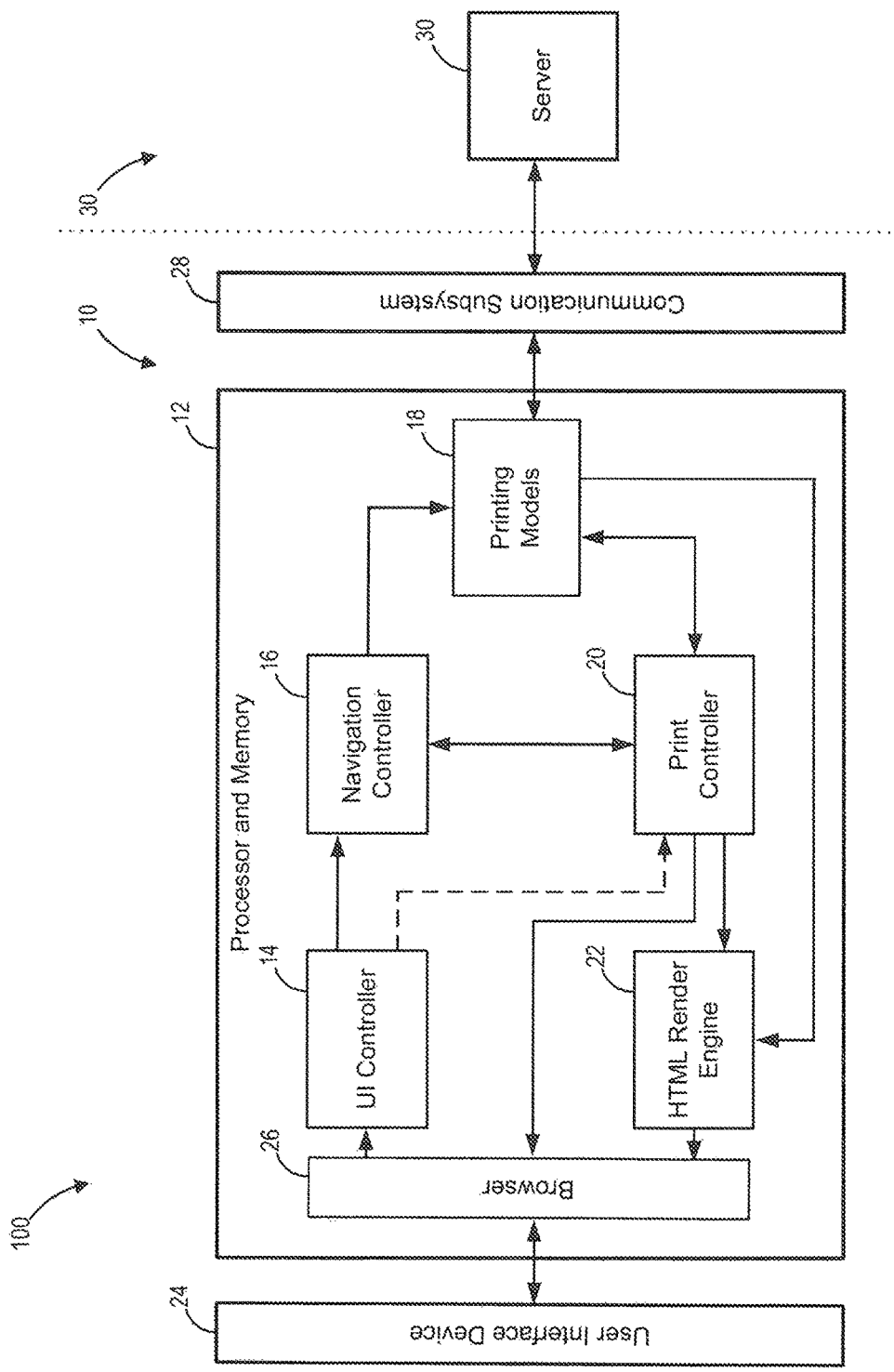
FIG. 1 is a block diagram of a system for printing medical images, according to at least one embodiment.

The skilled person in the art will understand that the drawings, described below, are for illustration purposes only. The drawings are not intended to limit the scope of the applicants' teachings in anyway. Also, it will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DESCRIPTION OF VARIOUS EMBODIMENTS

It will be appreciated that numerous specific details are set forth in order to provide a thorough understanding of the exemplary embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description is not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

The embodiments of the systems and methods described herein may be implemented in hardware or software, or a combination of both. However, preferably, these embodiments are implemented in computer programs executing on programmable computers, each comprising at least one processor, a data storage system (including volatile and non-volatile memory and/or storage elements), at least one input device, and at least one output device. For example and without limitation, the programmable computers may be a mainframe computer, server, personal computer, laptop, personal data assistant, cellular telephone, smartphone, or tablet device. Program code is applied to input data to perform the functions described herein and generate output information. The output information is applied to one or more output devices in known fashion.

Each program is preferably implemented in a high level procedural or object oriented programming and/or scripting language to communicate with a computer system. However, the programs can be implemented in assembly or machine language, if desired. In any case, the language may be a compiled or interpreted language. Each such computer program is preferably stored on a storage media or a device (e.g. ROM or magnetic diskette) readable by a general or special purpose programmable computer for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Furthermore, the system, processes and methods of the described embodiments are capable of being distributed in a computer program product comprising a computer readable medium that bears computer-usable instructions for one or more processors. The medium may be provided in various forms including one or more diskettes, compact disks, tapes, chips, wireline transmissions, satellite transmissions, internet transmission or downloadings, magnetic and electronic storage media, digital and analog signals, and the like. The computer-usable instructions may also be in various forms including compiled and non-compiled code.

Reference is now made to FIG. 1, which illustrates a block diagram of a system 100 for printing medical images, according to at least one embodiment. The system includes a client device 10 and a server 30. The client device 10 and the server 30 are in data communication with one another. The client device 10 and the server 30 can be located remotely from one another (indicated by dotted line).

The server 30 may include a data storage device to store medical studies, including medical images and information. The server 30 may further store an application that can be downloaded by the client device 10. The application can provide the client device with access to medical studies irrespective of the location of the medical studies. That is, the medical studies may be stored on another data storage device that is not the data storage device of the server 30.

Without limitation, the client device can be a mainframe computer, server, personal computer, laptop, personal data assistant, cellular telephone, smartphone or tablet device. The client device 10 includes a processor and memory (shown collectively as 12), a user interface device 24, and a communication subsystem 28. The communication subsystem 28 provides data communication between the client device 10 and other computer devices, such as the server 30.

The user interface device 24 allows a user to interact with the client device 10. A user may be any medical personnel such as clinicians, physicians, general practitioners, nurses, physician assistants, and receptionists. The user interface device 24 can be any device that allows the user to send commands to the processor and memory 12 and that communicates information to the user.

The user interface device 24 may include an output device and input device. For example, the output device can be a display monitor or screen for displaying an Internet browser 26. Furthermore, the Internet browser 26 may display medical studies, including medical images. The input device can be, but not limited to, a keyboard, a touch screen display, a stylus, a mouse, a dictation device, a voice recognition system, or a motion detection sensor. In some embodiments, the user interface device 24 can be a touch screen display that provides both input and output functions.

The application can be downloaded to the client device 10 for execution. In some embodiments, the application can be installed on the client device 10 for execution. The processor and memory 12 of the client device 10 can be configured to include a user interface (UI) controller 14, a navigation controller 16, printing models 18, a print controller 20, an HTML render engine 22, and an Internet browser 26. The UI controller 14 can interact with the Internet browser 26 to receive commands from the user interface device 24. Commands can include a selection or a deselection of a medical study, a series of medical images, or an individual medical image of a series of medical images for viewing and/or printing. Images can be individually selected or deselected. Images can be individually selected from a single series of medical images or a different series of medical images. As well, a series of medical images can be selected or deselected. In some embodiments, in the event that no medical images have been selected, the image currently displayed can be used as the selected medical image to be printed. While it is understood that an entire medical study, a plurality of medical studies, an entire series of medical images, a plurality of series of medical images, a single medical image, and plurality of medical images can be selected for viewing and/or printing, the description herein refers to any one of these selections as a "selection of medical images".

The UI controller 14 can also interact with the navigation controller 16 and the print controller 20. The UI controller 14 can provide the selection of medical images to the navigation controller 16. The UI controller 14 can also provide the selection of an image layout (i.e., number of columns of images on a page and a number of rows on a page, as described below) for the selection of medical images to the print controller 20.

The navigation controller 16 can receive the selection of medical images from the UI controller 14 and mark the medical images that have been selected. The navigation controller 16 can also interact with the models 18 and the print controller 20 to serve as the mechanism by which the print controller 20 navigates to each selected medical image for rendering. The navigation controller 16 can point to a selected medical image of the models 18. While the navigation controller 16 points to a selected medical image, the print controller 20 commands the HTML render engine 22 to render and display a page using the selected image layout and containing the selected medical image that is pointed to by the navigation controller 16 in the user interface device 24 by the Internet browser 26. The HTML render engine 22 updates the HTML page that the Internet browser 26 displays.

The navigation controller 16 can navigate to, or point to each medical image successively. That is, after pointing to a first selected medical image, the navigation controller 16 does not move to a second selected medical image of the models 18 until it receives indication from the print controller 20 that rendering of the first selected medical image is complete.

The models 18 interact with the communication subsystem 28 to receive the selected medical images from the server 30. The communication subsystem 28 can communicate with the server 30 over a network (not shown). In some embodiments, the communication between the client device 10, via the communication subsystem 28, and the server 30 can include web access to DICOM object (WADO) calls.

The models 18 can indicate to the print controller 20 that it has loaded a selected medical image indicated by the navigation controller 16. The models 18 can also provide to the print controller 20, print request information required for generating a model printable by the Internet browser. The print request information can include, but is not limited to, a paper size, header and footer information, side notes, and annotations. Annotations can include mark-ups, measurements, spatial transformations (e.g., pan, zoom, and/or rotation), and medical study or medical image attributes (e.g., orientation, image identification, and/or image index "x of n" with medical image series) to be applied or overlaid a medical image.

As described above, the print controller 20 can interact with the UI controller 14, the navigation controller 16, the models 18, and the HTML render engine 22. In addition, the print controller 20 can also interact with the Internet browser 26. The print controller 20 can provide information to the Internet browser 26 indicative of the progression of printing the medical images. The print controller 20 can also provide information to the Internet browser 26 indicative that the medical images are ready for printing. As well, the Internet browser 26 can flag when images have been loaded and are ready for printing. The print controller 20 can provide to the HTML render engine 22, an image layout to be rendered by the HTML render engine. The HTML render engine 22 updates the HTML page that the Internet browser 26 displays.

Figure 2:
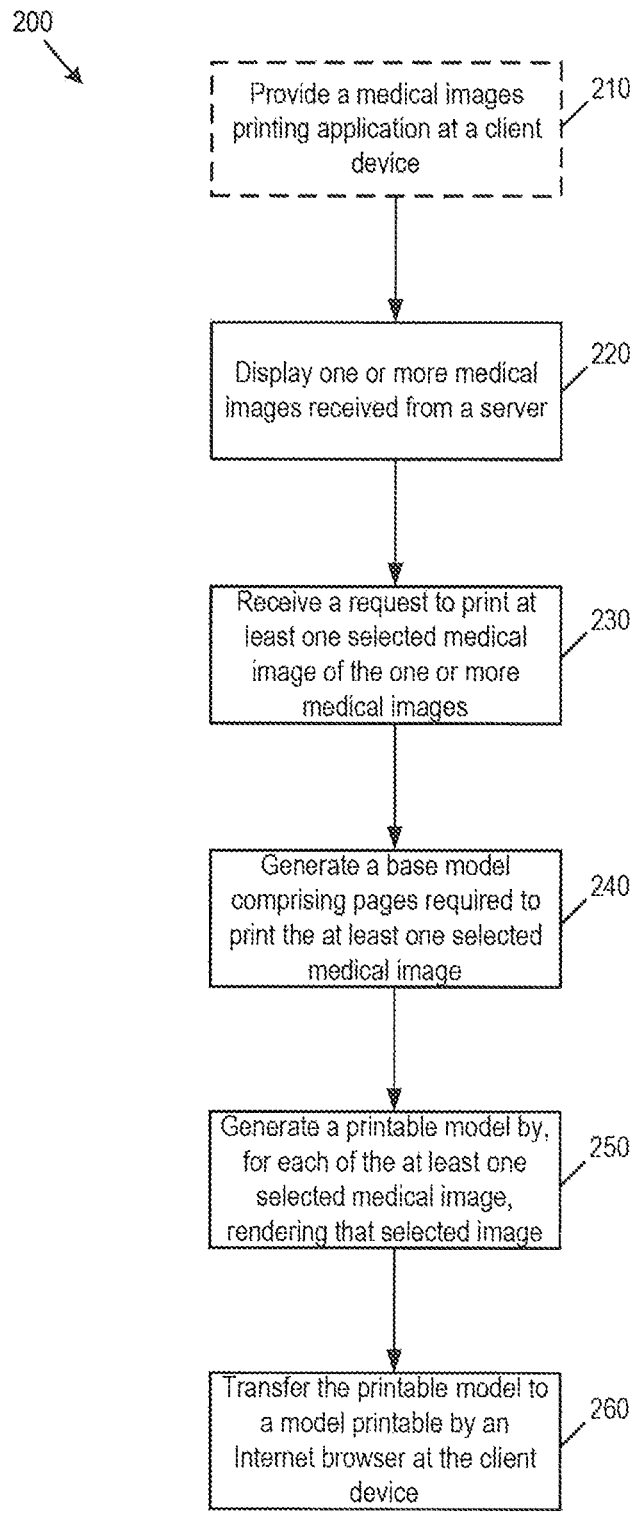
FIG. 2 is a flowchart illustrating a method of printing medical images, according to at least one embodiment.

Referring to FIG. 2, therein illustrated is a flowchart of a method 200 of printing medical images, according to at least one embodiment. In some embodiments, the method 200 can begin at step 210. At step 210, a medical images printing application can be provided to the client device 10. In some embodiments, the medical images printing application can be provided by the server 30 and downloaded to the client device 10 over a network (not shown). In some embodiments, the medical images printing application can be provided by a data storage device, such as a flash memory device, or a digital disc. At step 210, the medical images printing application can be executed on the client device 10.

After the medical images printing application is available on the client device 10, the method proceeds to step 220 in which one or more medical images are received from the server 30. The client device 10 can display the one or more medical images in an Internet browser. As shown by the graphical user interface 500 of FIG. 5A, a user at the client device 10 can view the one or more medical images from the Internet browser 26.

Figure 5A:
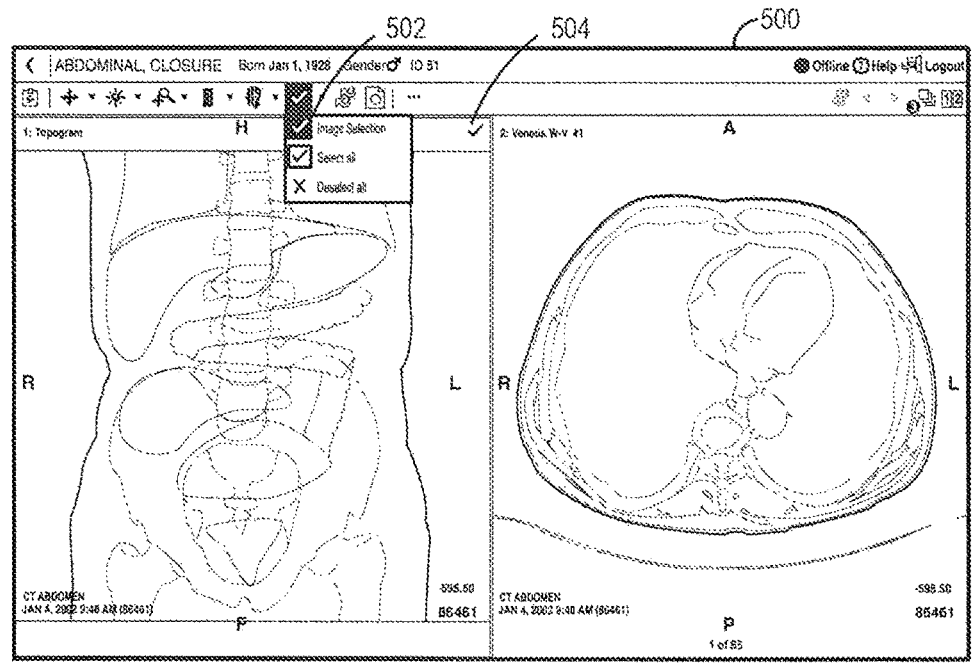
FIGS. 5A and 5B are illustrations of graphical user interfaces for selecting medical images to print, according to at least one embodiment.

After step 220, the method proceeds to step 230 when the client device 10 receives user input indicating a request to print at least one selected medical image of the one or more medical images displayed in the Internet browser 26. In some embodiments, the request to print selected medical images can be a request to print an entire series of medical images 502 (as shown in FIG. 5A). If a medical image is selected for printing, the graphical user interface can be updated to indicate 504 that a particular medical image has been selected for printing (as shown in FIG. 5A). The request to print at least one selected medical image can further include additional information that relate to, but are not limited to, side notes and annotations for a selected medical image, a selection of a paper size for the printout, a selection of image layout for the printout, and a selection of items to include in headers and footers.

Figure 5B:
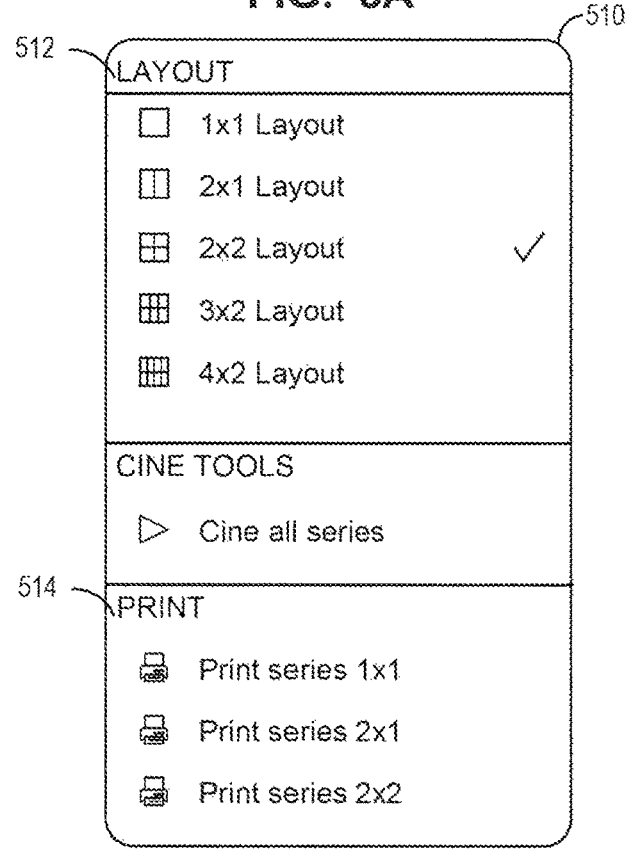

The medical images printing application can provide a limited number of paper sizes for the printout. The paper sizes can be standard paper sizes. Standard paper sizes can include sizes such as A4 and US Letter. The medical images printing application can provide a limited number of image layouts for the printout (as shown by print series selections 514 in graphical user interface 510 of FIG. 5B). Print series selections 514 are herein referred to as image layouts and relate to the layout of images on a single page. Image layouts can specify a number of columns of images on a page ("m") and a number of rows on a page ("n"). Example image layouts specified in an "m×n" format can include, but are not limited to, a 1×1 layout, a 2×1 layout, a 2×2 layout (as shown in FIG. 5B).

It should be noted that view layouts 512 are also shown in graphical user interface 510. View layouts relate to the display of medical images in the medical images printing application and do not relate to the layout of medical images in a printout. Example view layouts can include, but are not limited to, a 1×1 layout, a 2×1 layout, a 2×2 layout, a 3×2 layout, and a 4×2 layout.

Figure 4:
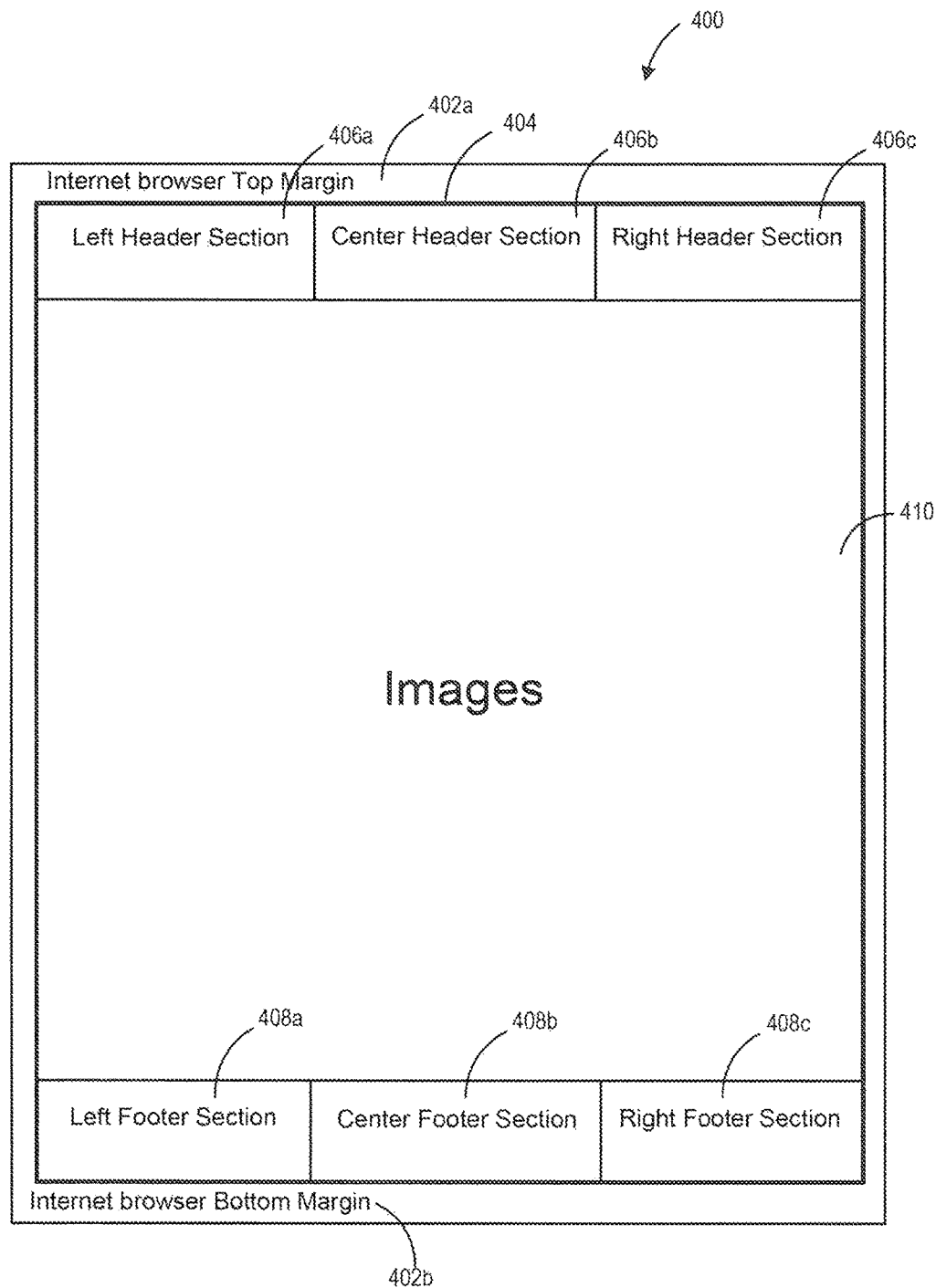
FIG. 4 is a schematic diagram of a base model for printing medical images, according to at least one embodiment.

The medical images printing application can provide a limited number of items to include in headers and footers. In some embodiments, headers and footers can each be further partitioned into different sections. FIG. 4 shows an example of a header that includes three sections: a left header section 406a, a center header section 406b, and right header section 406c. In some embodiments, a header may include two sections: a left header section and a right header section, a left header section and a center header section, or a center header section and a right header section. In some embodiments, a header may include only one section. Similarly, FIG. 4 shows an example of a footer that includes three sections: a left footer section 408a, a center footer section 408b, and right footer section 408c. In some embodiments, a footer may include two sections: a left footer section and a right footer section, a left footer section and a center footer section, or a center footer section and a right footer section. In some embodiments, a footer may include only one section.

In some embodiments, the header can have a different number of sections than that of the footer. For example, the header can include one section, and a footer can include three sections, namely a left footer section, a center footer section, and a right footer section. In some embodiments, the header and footer can have a same number of sections. When the header and footer have a same number of sections, the sections need not be similar. For example, a header can have a left header section and a center header section while a footer can have a center footer section and a right footer section. Alternatively, the header and footer can have similar sections. For example, the header can have a left header section and a right header section and the footer can also have a left footer section and a right footer section.

In some embodiments, headers and footers can include various fields for information that can include, but is not limited to, a patient name and/or initials, a patient identification number, a patient date of birth, a medical study description a medical image series description, a type of modality used to capture the medical image, a date and time of the medical image, an accession number, a requesting physician, etc. The height of the header and footers may vary, depending on the information that is requested to be included.

Figure 6A:
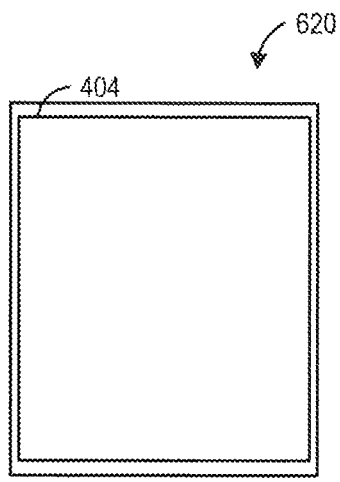
FIG. 6A to 6D are schematic diagrams of the general operational steps of generating a printable model for printing medical images, according to at least one embodiment.

Upon receiving the request to print at least one selected medical image at step 230, the method proceeds to step 240. At step 240, a base model is generated. As shown in FIG. 6D, the base model 626 includes at least one page required to print the at least one selected medical image requested by the user. One or more pages may be required to print the at least one selected medical image requested by the user. However, each page of the base model is identical. In some embodiments, each page has a set of elements relating to the layout of the page. When the base model includes more than one page, each of the pages have identical elements. That is, each of the pages have identical layouts. The location and dimensions of elements on a page of the base model are the same as the location and dimensions of elements on any other page of the base model.

In some embodiments, elements can relate to, but are not limited to, placeholders for headers, footers, and images. Elements for images, herein referred to as image elements provide a space, or area, in which images can be placed. In contrast, elements for headers, herein referred to as header elements, can provide a space, or area, in which information can be placed. Similarly, elements for footers, herein referred to as footer elements, can provide a space, or area, in which information can be placed. Furthermore, as set out above, headers and footers can be partitioned to different sections. Accordingly, elements for headers can include header section elements and elements for footers can include footer section elements.

After step 240, the method proceeds to step 250. At step 250, a printable model is generated using the base model of step 240. The printable model includes each of the selected medical images. Each medical image can be rendered to an image element of a page of the base model. More specifically, each medical image can be rendered to a placeholder for an image of a page of the base model. The rendered medical image is scaled to fit the size of the image element.

Figure 7A:
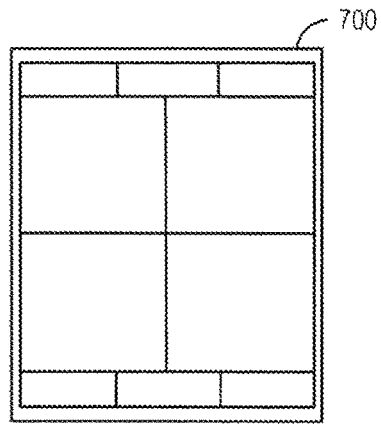
FIG. 7A to 7F are schematic diagrams of the general operational steps of generating a base model for printing medical images, according to at least one embodiment.
Figure 7B:
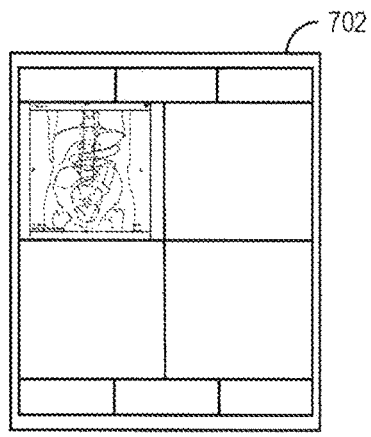
Figure 7C:
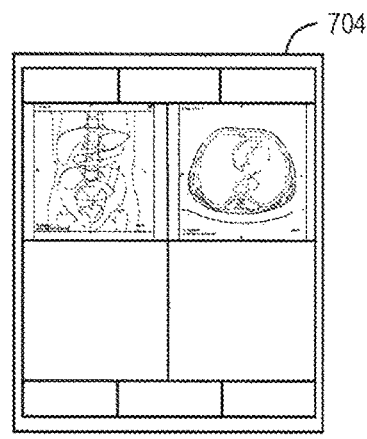

Referring to FIGS. 7A to 7C, therein shown is a base model 700 in FIG. 7A. No medical images are included in the base model 700. As shown in 702 of FIG. 7B, a first selected medical image can be rendered to a first image element. After the first selected medical image is rendered to the first image element, a second selected medical image can be rendered to a second image element, as shown in 704 of FIG. 7C.

Returning to FIG. 2, after step 250 the method 200 proceeds to step 260. At step 260, the printable model of step 250 is transferred to a model printable by the Internet browser 26. After the printable model is transferred to a model printable by the Internet browser, the printing function of the Internet browser 26 can be used to generate printouts.

Figure 7D:
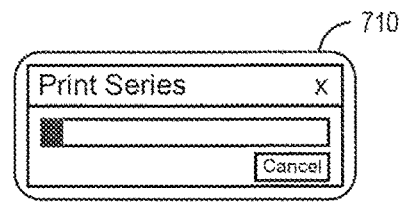
Figure 7E:
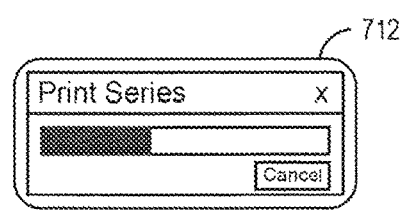
Figure 7F:
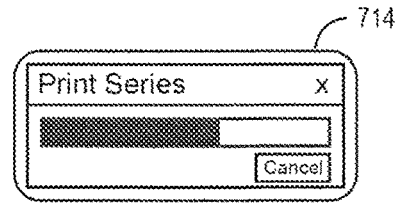

In some embodiments, the medical images printing application can provide a progress meter to indicate the progress of the print request of the at least one selected medical image. As shown in FIG. 7A to 7F, the progress meter includes a bar that is proportional to the number of images that are rendered to the printable model. The progress meter 710 in FIG. 7D shows little progress because it corresponds to the base model 700 in FIG. 7A, which does not contain any rendered medical images yet. The progress meter 712 in FIG. 7E shows some progress because it corresponds to a printable model 702 in FIG. 7B, which is in progress, or partially complete with one rendered medical image. The progress meter 714 in FIG. 7F shows further progress because it corresponds to a printable model 704 in FIG. 7C with two rendered medical images. In some embodiments, a progress meter may not be provided when only one medical image is selected for printing.

Figure 3:
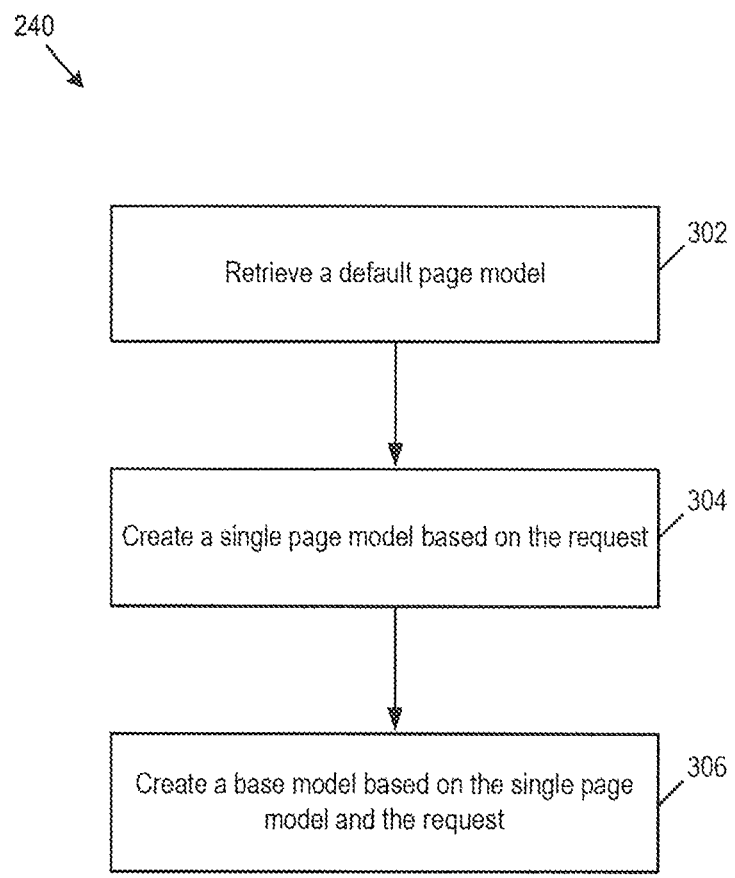
FIG. 3 is a flowchart illustrating general operational steps of generating a base model for printing medical images, according to at least one embodiment.

Referring to FIG. 3, therein illustrated is a flowchart of a method of generating a base model in step 240, according to at least one embodiment. In some embodiments, generating a base model involves first retrieving a default page model at step 302. As shown in FIG. 6A, the default page model 620 includes a printable area element 404. The printable area element 404 can relate to the area printable by the Internet browser 26. The area printable by the Internet browser 26 can vary with the Internet browser 26 used by the user. Generally, an Internet browser 26 reserves space for margins and does not print a web page in the space reserved for margins. That is, the printable area element 404 can relate to space not reserved, or not allocated, to the Internet browser margins. In some embodiments, the Internet browser margin includes an Internet browser top margin 402a and an Internet browser bottom margin 402b, as shown in FIG. 4. In some embodiments, the Internet browser margin further includes an Internet browser left margin located at a left edge of the page and an Internet browser right margin located at a right edge of the page. Since the medical images printing application may be used with more than one Internet browsers, the area printable by the Internet browser can be defined by the largest Internet browser top margin 402a, the largest Internet browser bottom margin 402*b*, the largest Internet browser left margin, and the largest Internet browser right margin. That is, the area printable by the Internet browser can be assumed to be the smallest area printable by any combination of Internet browsers.

The printable area element 404 can be pre-defined, having an associated height and associated width. In some embodiments, the associated height and associated width of the printable area element 404 can vary with the selection of a paper size for the printout, that is, the paper size selection. Accordingly, retrieving a default page model 620 can be based on the paper size selection.

In some embodiments, retrieving a default page model 620 at step 302 involves determining whether a default page model exists. In some embodiments, the default page model may exist if the current instance of the medical images printing application has already been used to print selected medical images. Where the default page model already exists, the default page model can be stored in random access memory (RAM) of the client device 10. If a default page model does not exist, a default page model can be created. The default page model can be created and stored in the client device 10 RAM.

After step 302, the method proceeds to step 304. At step 304, a single page model based on the request can be created. The single page model can include the default page model 620 retrieved in step 302. That is, the single page model can include the printable area element 404 of the default page model 620.

To create the single page model, an image area 410 is determined based on the printable area element 404 of default page model 620 and the request. The image area 410 includes an image area width and an image area height. The image area 410 is contained within, or overlaps with, the printable area element 404.

In some embodiments, the image area width can be the same as the associated width of the printable area element 404. In some embodiments, the request can include side notes to be located adjacent to the Internet browser left margin and/or an Internet browser right margin. In such cases, the image area width can be smaller than that of the associated width of the printable area element 404.

In some embodiments, the image area height can be the same as the associated height of the printable area element 404. The image area height can be the same as the associated height of the printable area element 404 when the request specifies no header and no footer.

In some embodiments, the request can include a header, a footer, or both a header and a footer. When the request includes a header and/or a footer, the image area height can vary depending on the height of the header and/or footer. The height of the header and/or footer can vary, depending on the font, the spacing, and the information provided in the header and/or footer. For example, a request can indicate that the header includes a patient name, a patient identifier, a study date, a study description, and a series description, a height of the header can be determined to provide space for, or to accommodate this information. When the request indicates that the header further includes a patient birthdate and the requesting physician, the height of the header can be determined to accommodate this information as well. The height of the header in the later example with a patient birthdate and requesting physician can be larger than the height of the header in the former example without the patient birthdate and requesting physician.

Figure 6B:
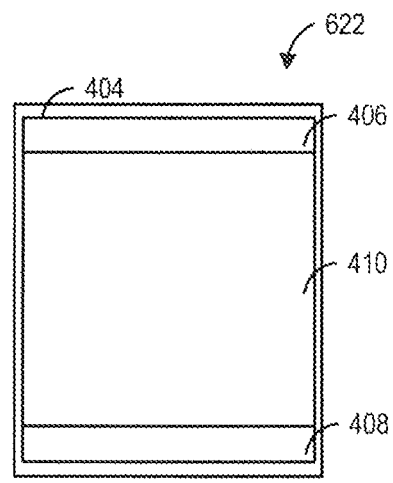

The height of the header and/or footer can be measured using a test model 622 shown in FIG. 6B. The test model 622 can be created using the default page model 620, which includes printable area element 404. A header element 406 and a footer element 408 can be added to the test model. Each of the header element 406 and the footer element 408 of the test page 622 can be contained within, or overlap with, the printable area element 404. The header element 406 is generally located along a top edge of the printable area element 404 while the footer element 408 is generally located along a bottom edge of the printable area element 404. Each of the header element 406 and the footer element 408 of the test page can have an associated height that remains undefined so that they will be rendered at their natural height, based on the font, the spacing, and the information specified in the request.

After the test model 622 is created, the test model 622 can be rendered to a document object model (DOM) of the Internet browser 26. After the test model 622 is rendered, a shortest distance between the header element 406 and the footer element 408 in the DOM can be determined. In some embodiments, the shortest distance between the header element 406 and the footer element 408 can be measured. In some embodiments, the height of each of the header element 406 and the footer element 408 can be measured. When the height of each of the header element 406 and the footer element 408 are measured, the shortest distance between the header element 406 and the footer element 408 can be determined by subtracting the height of the header element 406 and the footer element 408 from the height of the printable area element 404. The image area height in the single page model can be determined based on the shortest distance between the header element and the footer element in the DOM.

As set out above, the request can include a selection of an image layout for the printout. When a selection of an image layout includes more than one image per page, step 304 involves adding more than one image elements to the single page model 624 shown in FIG. 6C. In particular, one image element is added for each image to be printed on a page. Image elements are added to the image area 410. However, image elements do not overlap. That is, space allocated to a first image element is not also allocated to a second image element. Accordingly, the image area height is distributed amongst the number of image rows per page specified by the request. That is, each image element has a height that corresponds to the image area height divided by the number of image rows per page. Similarly, the image area width is distributed amongst the number of image columns per page specified by the request. Each image element has a width that corresponds to the image area width divided by the number of image columns per page.

Figure 6C:
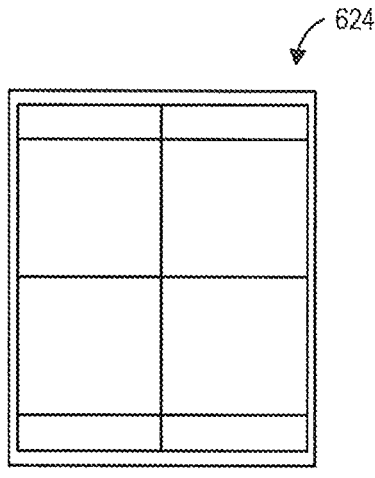
Figure 6D:
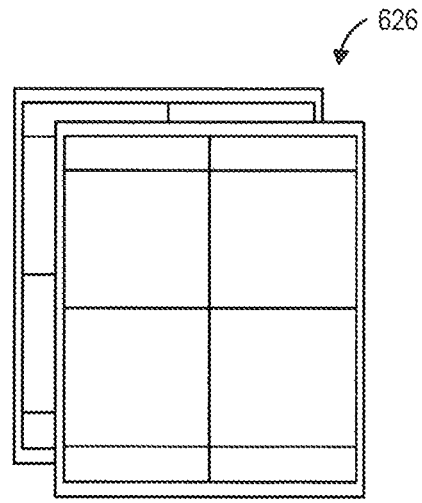

Referring to FIG. 6C, therein shown is an example single page model 624 that includes four image elements. In this example, the request indicated a 2×2 image layout selection. Accordingly, each image element has width that corresponds to half of the image area width and each image element has a height that corresponds to half of the image area height.

As set out above, in some embodiments, the request can indicate that the printouts should include or exclude headers and footers, different sections within the headers and footers, and/or various fields for information. At step 304, header section elements and footer section elements can be added to the single page model 624, based on the request. Image elements, header section elements, and footer section elements do not overlap. That is, space allocated to an image element is not also allocated to header section elements or footer section elements. Space allocated to a header section element is not also allocated to the footer section element.

Referring to FIG. 6C, therein shown is an example single page model 624 that includes two sections for each of the footer and header. In this example, the request indicated that each of the header and footer includes two sections. The request further indicated that the width of each header section is a half of the total horizontal area of the header and the width of each footer section is a half of the total horizontal area of the footer. In some embodiments, total horizontal area of each of the header and the footer can be the same as the associated width of the printable area element 404. In some embodiments, the total horizontal area of each of the header and the footer can be less than the associated width of the printable area element 404. The total horizontal area of each of the header and the footer can be less than the associated width of the printable area element 404 when the request also includes side notes to be located adjacent to the Internet browser left margin and/or an Internet browser right margin.

In another example, the request can indicate that a footer is included and the footer includes three sections: a left section, a center section, and a right section. In some embodiments, each footer section may have a width of a third (⅓) of the horizontal area. In some embodiments, the left footer section and the right footer section can have a width of a quarter (¼) of the horizontal area and center footer section can have a width of a half (½) of the horizontal area. In contrast, FIG. 6C shows an example in which the request indicates that the footer includes two footer sections and each section has width of a half (½) of the horizontal area. If the request indicates that the footer includes only one section, the footer section may have a width of the entire horizontal area. Each section of the header can be similarly allocated a horizontal area based on the number of sections of the header indicated by the request.

After step 304, the method proceeds to step 306. At step 306, a base model is created using the single page model of step 304 and the request. A base model 626 is shown in FIG. 6D. The base model 626 includes the single page model, replicated, or duplicated, by some number that corresponds to the number of pages required for the number of selected medical images For example, with a 2×2 image layout, each page includes four image elements. If 3 medical images are selected for printing, the base model would include 1 page. If 5 medical images are selected for printing, the base model 626, as shown in FIG. 6D includes 2 pages. In another example, if 5 medical images and a 3×2 image layout is selected for printing, the base model would only include 1 page. After step 306, a base model is generated and the method returns to step 250 of method 200 in FIG. 2.

Figure 8:
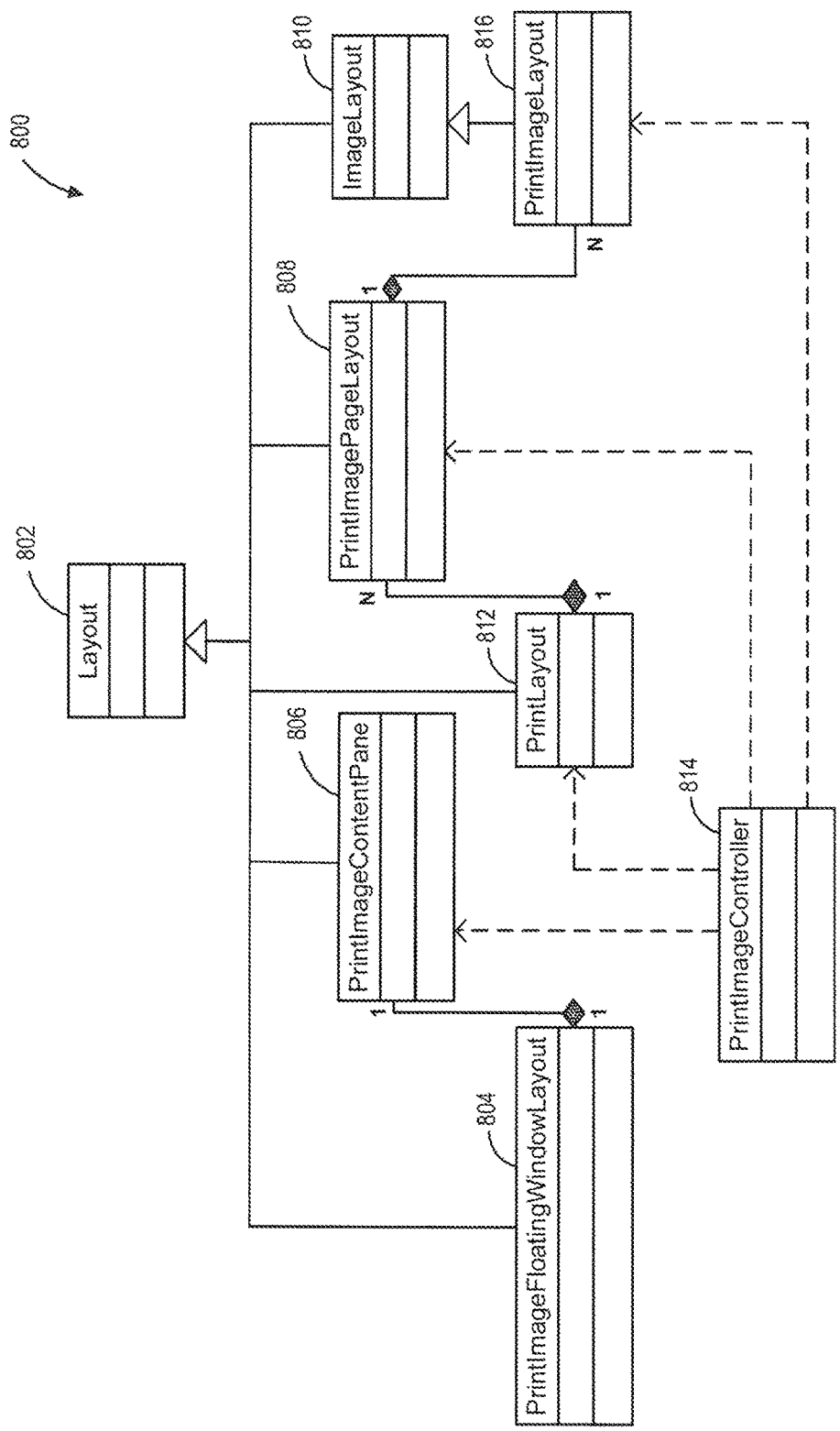
FIG. 8 is a schematic diagram of components of a medical images printing application, according to at least one embodiment.

Referring to FIG. 8, therein shown are components 800 of a medical images printing application, according to at least one embodiment. Each of the PrintImageFloatingWindowLayout 804, PrintImageContentPane 806, PrintLayout 812, PrintImagePageLayout 808, and ImageLayout 810 can be extensions of the Layout 802 component. The PrintImageFloatingWindowLayout 804 and the PrintImageContentPane 806 can together provide a progress meter shown in FIGS. 7D to 7F. The PrintImageFloatingWindowLayout 804 can provide a container for the PrintImageContentPane 806.

The PrintLayout 812 can provide and maintain the base model generated in step 240 of method 200 in FIG. 2. As set out above, base model includes the pages required to print the at least one selected medical image. The PrintLayout 812 can instantiate and contain a PrintImagePageLayout 808 for each page of the base model. That is, a single PrintLayout 812 instantiates a plurality (N) of PrintImagePageLayouts 808. The plurality of PrintImagePageLayouts 808 instantiated relates to the number of pages of the base model, or the number of pages required for the print request.

The PrintImageLayout 816 can be used to generate the printable model by rendering a selected medical image to an image element of the base model. The PrintImageLayout 816 provides a single image rendering object. To render a plurality of selected medical images, the PrintImageLayout 816 can be reused to render each of the plurality of selected medical images to the base model successively. As shown in FIG. 8, the PrintImageLayout 816 can be an extension of the ImageLayout 810. The ImageLayout 810 renders images to be displayed on the user interface device 24.

The PrintImageController 814 can control and manage steps of the printing process from initialization to finalization. A new PrintImageController 814 can be instantiated for a new print request. In particular, the PrintImageController 814 can monitor various events to ensure that the printing process is executed properly. For example, in some embodiments, the PrintImageController 814 can identify user input indicative of a cancellation of the printing process, arrival of an image that is ready for rendering to the printable model, a printable model that is ready to be transferred to an Internet browser, and the completion of the printing request. By identifying these events, the PrintImageController 814 can update the progress meter via the PrintImageContentPane 806, assign the user selected image layout to the PrintLayout 812, measure and set the reallocated height of the header element and footer element, render the PrintLayout 812 to the DOM, dispose of the PrintLayout 812 settings and Layout 802 descendants, set up the navigation to individual images using the PrintImageLayout 816, and manages the rendering of individual images using the PrintImagePageLayout 808.

Figure 9:
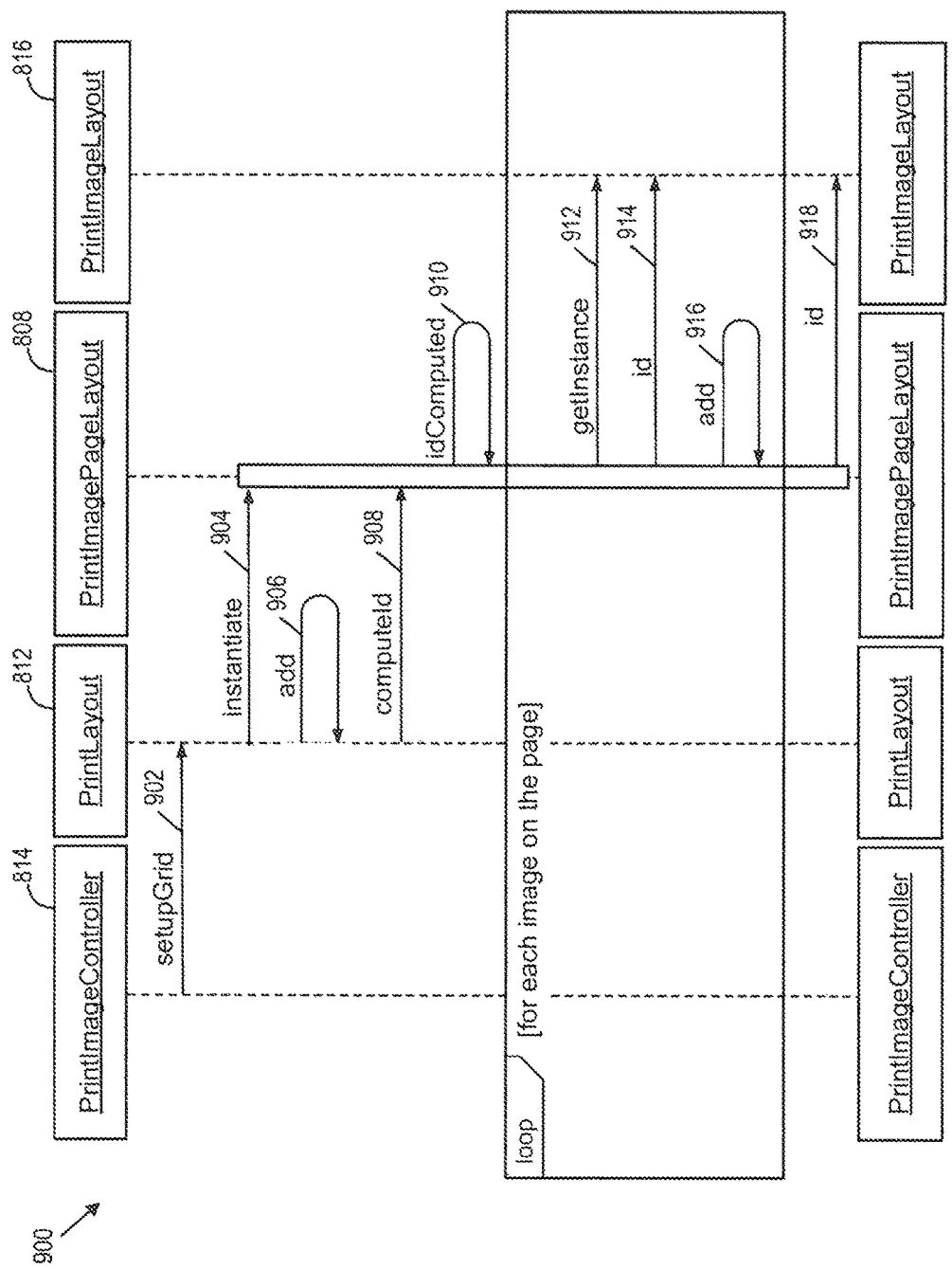
FIG. 9 is an event diagram illustrating general operational steps taken by the components of a medical images printing application of FIG. 8 for generating a printable model for printing medical images, according to at least one embodiment.

FIG. 9 is an event diagram illustrating general operational steps taken by the components of a medical images printing application of FIG. 8 for generating a printable model for printing medical images, according to at least one embodiment. The method 900 can begin at step 902 when the PrintImageController 814 receives a request to print selected medical images. Upon receiving the request, a default page model can be retrieved. Step 902 can involve the PrintLayout 812 calculating the number of pages based on the image layout selection and the number of selected medical images. Step 902 can also involve setting up, or initiating the header element and footer element.

After step 902, the method proceeds to step 904. At steps 904 to 910, a base model can be generated by duplicating the default page model based on the image layout selection and number of selected medical images determined at step 902. Steps 904 to 910 can involve instantiating the PrintImagePageLayout 808 for each page to print, adding each PrintImagePageLayout 808 as a child of the PrintLayout 812, generating an identifier for each PrintImagePageLayout 808 that is added as a child, and calling the identifier for each child.

After the base model is generated, the method can proceed to step 912. At steps 912 to 916, a printable model can be generated by looping through each image element on each page of the base model. On each page, an identifier for each single image rendering object (i.e., the PrintImageLayout 816) can be added to an image element of that page.

After step 918, the printable model is generated. Since all selected medical images have been added to the printable model, the single image rendering object is no longer required and an identifier for the PrintImageLayout 816 can be nulled out.

Figure 10A:
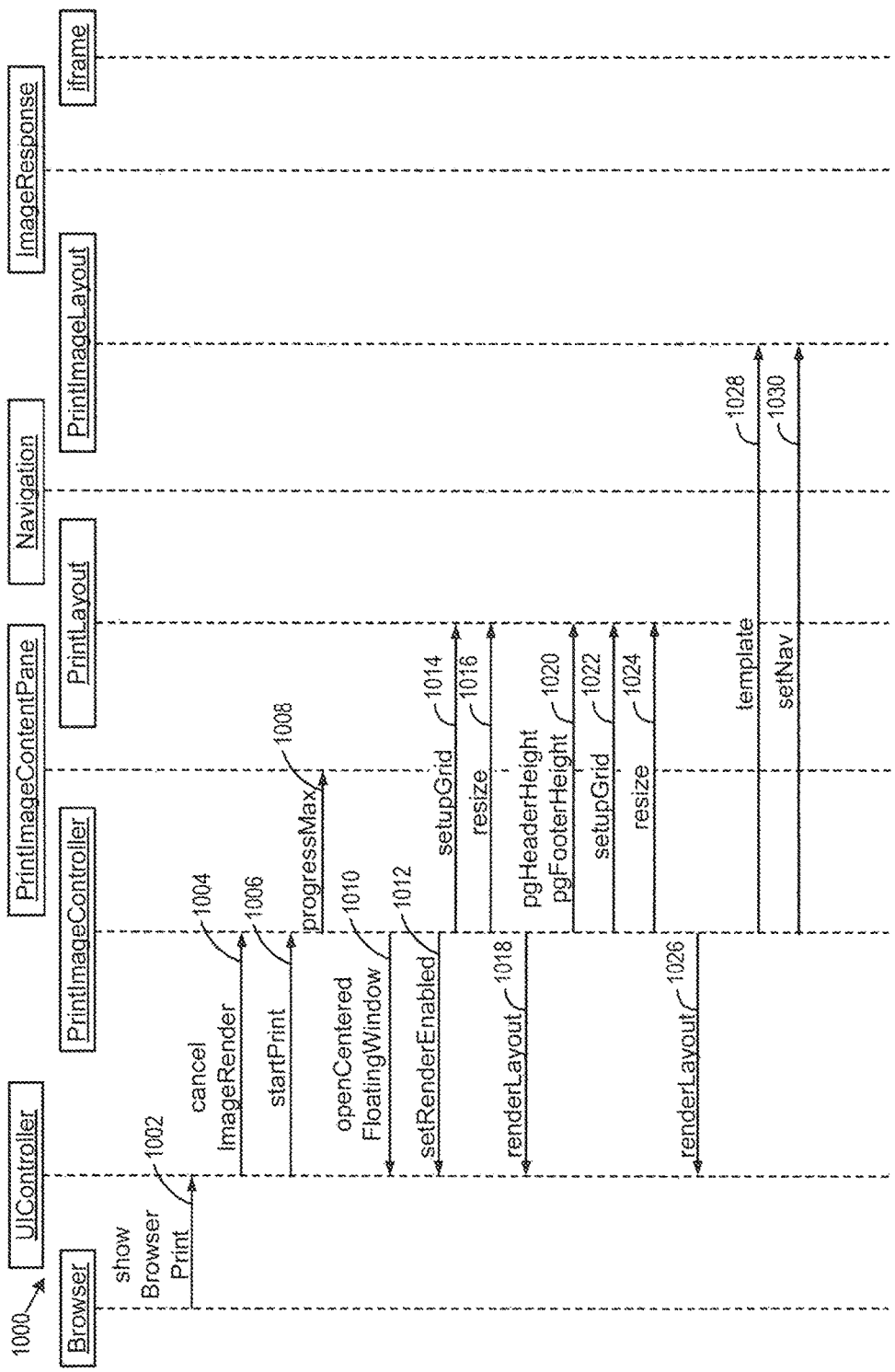
FIG. 10A to 10C is an event diagram illustrating a method of printing medical images by the components of a medical images printing application of FIG. 8, according to at least one embodiment.
Figure 10B:
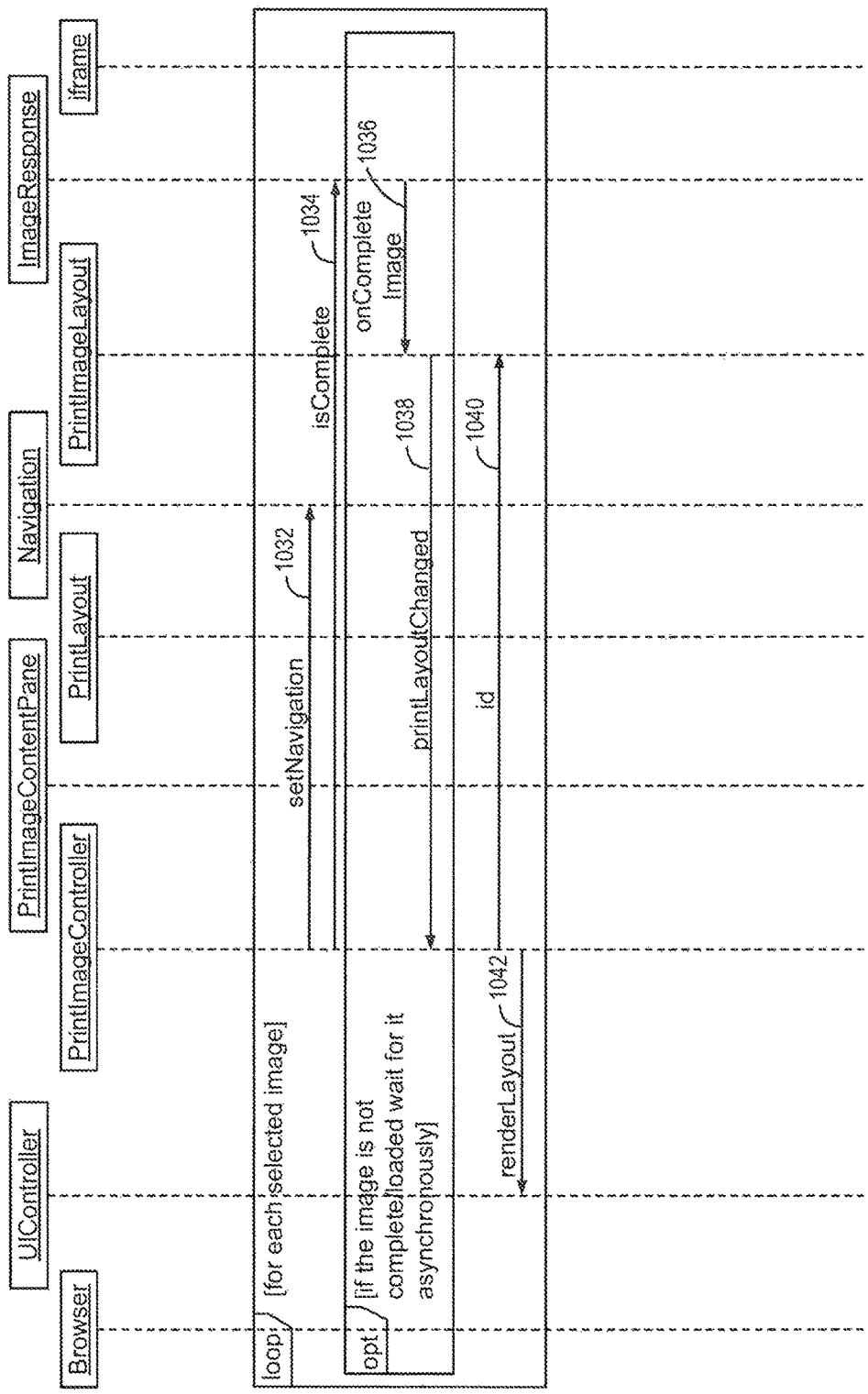
Figure 10C:
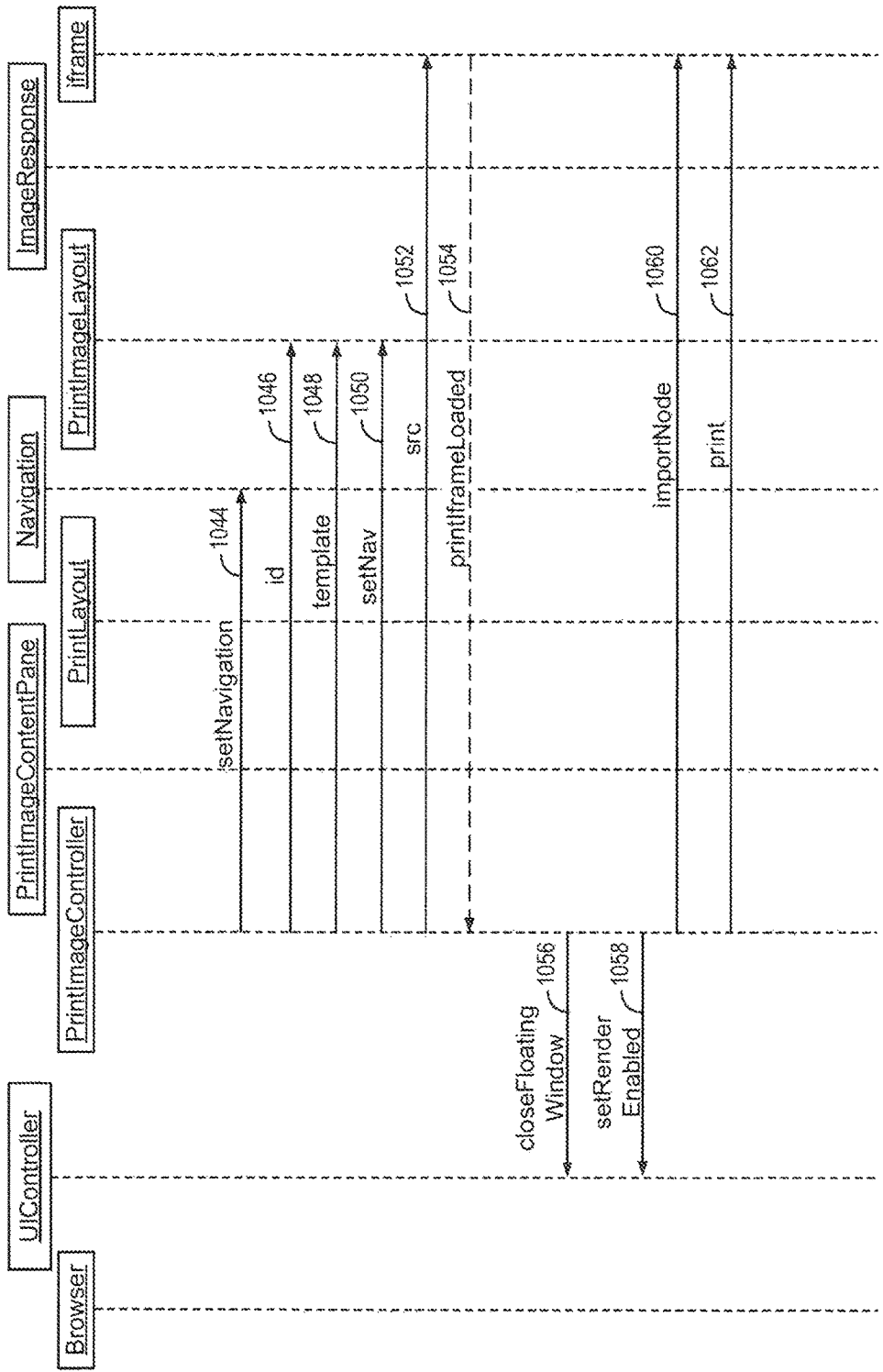

FIG. 10A to 10C is an event diagram illustrating a method of printing medical images by the components of a medical images printing application of FIG. 8, according to at least one embodiment. The method 1000 can begin at step 1002 when the user selects an image layout to print selected medical images from the Internet browser 26. Upon receiving the request, the UI controller 14 can cancel any pending or active print requests in which images are being rendered at step 1004 and begin a new printing process at step 1006.

At step 1008, the PrintImageController 814 can instantiate the PrintImageContentPane 806 to initialize a progress meter based on the number of medical images selected for the print request. In particular, the maximum of the progress meter is dependent upon the number of medical images selected for the print request. At step 1010, the PrintImageController 814 can open a floating window to display the progress meter. Initially, the progress meter can have a value of zero.

At step 1012, the PrintImageController 814 can turn off any rendering that might occur to ensure that the PrintImageController controls all rendering during the printing process. This is required because rogue renders cannot be handled gracefully while rendering for printing occurs. An example of rogue rendering is rendering due to resizing the Internet browser window. By turning off any all other rendering, rogue renders are deferred until after the print request has completed.

After step 1012, the method 1000 proceeds to determining the image area 410. At step 1014, the PrintImageController 814 can set the image layout in the PrintLayout 812 on each page to be 1×1. Step 1014 is the first of three steps for rendering a single page model with no images in order to measure the header and footer Cascading Style Sheet (css) height and then allocate the header and footer height in the single page model.

At step 1016, the PrintImageController 814 can resize the height of the header element and the height of the footer element in the PrintLayout 812 to a value of zero. Resizing the height of the header element and the footer element in the PrintLayout 812 to a value of zero allows for the determination of the height of the area for the images. In some embodiments, this header and footer height resizing does not affect the sizing of the header and footer in the HTML because the height for the header and footer is not specified in the DOM. Furthermore, the header and footer height resizing is not displayed to the user by the Internet browser 26 because the Internet browser 26 will render the header and footer at their natural height.

At step 1018, the PrintImageController 814 can render the PrintLayout 812 and its contents to the DOM. Since the PrintLayout 812 is rendered to the DOM, the view of the PrintLayout 812 remains hidden and is not displayed in the Internet browser 26. That is, step 1018 does not have a visual effect.

At step 1020, the PrintImageController 814 can retrieve the header and footer elements of the single page model from the DOM and extract the height of the header and footer elements. In some embodiments, the height of the header and footer elements can be determined using a function such as offsetHeight. Having determined the height of the header and footer elements, the PrintImageController 814 can set these values for the PrintLayout 812 and its descendants to use.

At step 1022, the PrintImageController 814 can set the image layout on every page to the image layout selected by the user. Step 1022 can establish the number of pages to be printed.

At step 1024, the PrintLayout 812 and its descendants can be resized to fit the image layout to the space available on each page, or the image area 410. The image area 410 on each page is based on the printable area 404 less the space allocated for the header and the footer. The printable area 404 is based on the space on a page and not allocated to the Internet browser margins, such as the Internet browser header section 402a and the Internet browser footer section 402b.

At step 1026, the PrintLayout 812 and its descendants are rendered to the DOM. Similar to step 1018, step 1026 does not have a visual effect. The PrintLayout remains hidden and is not displayed in the Internet browser 26. Furthermore, the PrintLayout 812 rendered in step 1026 does not include any images. Each reference in the PrintLayout 812 to the PrintImageLayout 816 renders a blank slot because the view for PrintImageLayout 816 remains empty.

Various steps can be taken at 1028 to 1030 in order to utilize the single image rendering object. At step 1028, the template for the single image rendering object is set. At step 1030, the navigation controller 16 is set to a first selected medical image for the single image rendering object.

At steps 1032 and 1034, the PrintImageController 814 iterates over the selected medical images of the active series. More specifically, the active series can be an ordered set of one or more selected medical images. At step 1032, for each selected medical image of the ordered set, the PrintImageController 814 can navigate to that selected medical image and notify the single image rendering object. The single image rendering object, that is the PrintImageLayout 816, can then perform calculations to scale the image to fit the image element so that the image is rendered properly. After the PrintImageLayout 816 begins loading an image to print, at step 1034, the PrintImageController 814 checks whether the image has been loaded.

If the PrintImageController 814 determines that the image has not been loaded, then the PrintImageController 814 can relinquish control back to the Internet browser 26 and wait to be notified of when the image is loaded. At step 1036, notification that the image is loaded can be received from by the PrintImageLayout 816, which can in turn, notify the PrintImageController 814 at step 1038.

If the PrintImageController 814 determines that the image has been loaded, the identifier of the single image rendering object is set to an appropriate image element in the PrintLayout 812 at step 1040 in order to render the image at step 1042. Step 1042 can further involve updating the progress meter. More specifically, the progress meter can be updated to indicate that one selected medical image has been rendered.

Steps 1032 to 1042 are reiterated for each subsequent selected medical image of the ordered set of one or more selected medical images to generate the printable model. By reiterating through steps 1032 to 1042, the single image rendering object is reused to render each of the at least one selected medical image to an image element. Furthermore with steps 1036 and 1038, each subsequent selected medical image is not rendered until a previous selected medical image has been rendered. By successively reusing a single image rendering object for each selected medical image, less memory is used than using an image rendering object for each selected medical image.

The printable model is generated after all the selected images have been rendered. At steps 1044 to 1050, the navigation controller 16 can be restored to its initial configuration prior to step 1028. More specifically, at step 1044, the navigation controller 16 can be restored to its original position prior to being set to the first selected medical image for the single image rendering object at step 1030. The single image rendering object is no longer required and an identifier for the PrintImageLayout 816 can be set to a null value at step 1046. At step 1048, the original template of the PrintImageLayout 816 can also be restored to the template prior to step 1028. At step 1050, the single image rendering object can be removed from the navigation controller 16.

At step 1052, an iframe element can be created and added to the DOM. The src of the iframe element, that is the address of the iframe element, is set to a document with an empty body to be used for printing.

After the iframe element is added to the DOM and loaded, the iframe can notify the PrintImageController 814 at step 1054. Upon notification that the iframe element is loaded, the PrintImageController 814 can close the progress meter at step 1056. At step 1058, any other rendering, which were previously turned off at step 1012, are restored.

At step 1060, the PrintImageController 814 can import the DOM view corresponding to the PrintLayout 812 into the iframe document. That is, the printable model can be transferred to a model printable by Internet browser 26. Once all the images have been loaded into the iframe, the PrintImageController 814 can instruct the Internet browser 26 to print the iframe document at step 1062.

By first generating a printable model and then transferring the printable model to a model printable by the Internet browser 26, additional memory can be required compared to directly generating a printable model that is also printable by the Internet browser 26. However, the increase in memory requirements is temporary and only persists during the printing process. Furthermore, the two-step process permits use of existing HTML render engines 22 without modifications.

Numerous specific details are set forth herein in order to provide a thorough understanding of the exemplary embodiments described herein. However, it will be understood by those of ordinary skill in the art that these embodiments may be practiced without these specific details. In other instances, well-known methods, procedures and components have not been described in detail so as not to obscure the description of the embodiments. Furthermore, this description is not to be considered as limiting the scope of these embodiments in any way, but rather as merely describing the implementation of these various embodiments.

The invention claimed is:

1. A computer-implemented method of printing medical images, the method comprising:
   a) displaying, in an Internet browser at a client device, one or more medical images received from a server;
   b) receiving, at the client device, a request to print at least one selected medical image of the one or more medical images;
   c) in response to receiving the request, generating, at the client device, a base model comprising at least one page required to print the at least one selected medical image, each page of the base model having identical image elements as any other page of the base model;
   d) generating, at the client device, a printable model by, for each of the at least one selected medical image, rendering that selected image to an image element of a page of the base model; and
   e) transferring the printable model to a model printable by the Internet browser;

wherein:
   the generating a base model comprises:
      a) retrieving a default page model to print at least one selected medical image of the one or more medical images, the default page model comprising a printable area element;
      b) creating a single page model based on the request by determining an image area based on the printable area element of the default page model and the request, the image area comprising an image area width and an image area height, the single page model comprising the default page model and at least one of an image element, a header section element, and a footer section element, each of the at least one of the image element, the header section element, and the footer section element comprising area allocated to the printable area element; and
      c) creating a base model based on the single page model and the request;
   the determining an image area based on the printable area element of the default page model and the request comprises determining the image area height by:
      a) creating a test model comprising the default page model, a header element and a footer element, the header element comprising area allocated to the printable area element and located along a top edge of the printable area element, the header element having an associated height based on the request, the footer element comprising area allocated to the printable area element and located along a bottom edge of the printable area element, the footer element having an associated height based on the request;
      b) rendering the test model to a document object model of the Internet browser;
      c) measuring, from the document object model having the test model, a shortest distance between the header element and the footer element; and
      d) determining the image area height based on the shortest distance between the header element and the footer element.

2. The method of claim 1, wherein:
   a) the method further comprises providing a medical images printing application at the client device, the medical images printing application comprising a single image rendering object; and
   b) the generating, at the client device, a printable model by, for each of the at least one selected medical image, rendering that selected image to an image element of a page of the base model comprises reusing the single image rendering object to render each of the at least one selected medical image to an image element of the base model.

3. The method of claim 2, wherein:
   a) the at least one selected medical image comprises an ordered set of one or more selected medical images, the ordered set of one or more selected medical images comprising a first selected medical image and one or more subsequent selected medical images, each of the subsequent selected medical images having a corresponding previous selected medical image; and
   b) the reusing the single image rendering object to render each of the at least one selected medical image to an image element of the base model comprises for each subsequent selected medical image, rendering the subsequent selected medical image after the corresponding previous selected medical image has been rendered.

4. The method of claim 1, wherein the rendering a selected image to an image element of the base model comprises scaling the selected image to fit the image element.

5. The method of claim 1, further comprising:
a) upon receiving the request to print the at least one selected medical image of the one or more medical images, initializing a progress meter; and
b) for each of the at least one selected medical image, upon rendering that selected image to an image element of the base model, updating the progress meter to indicate an amount of selected medical images that have been rendered.

6. The method of claim 1, wherein the model printable by the Internet browser comprises a document object model of an Internet browser frame.

7. The method of claim 6, wherein the method further comprises loading a new Internet browser frame at the client device; and the Internet browser frame to which the printable model is transferred to is the new Internet browser frame.

8. The method of claim 1, further comprising after transferring the printable model to a model printable by the Internet browser:
a) providing notification, at the client device, that the request is ready for printing using the Internet browser;
b) receiving, at the client device, a confirmation to print the model printable by the Internet browser; and
c) sending the model printable by the Internet browser to a printer at the client device.

9. The method of claim 1, wherein the retrieving a default page model further comprises:
a) determining that a default page model does not exist; and
b) creating a default page model.

10. The method of claim 1, wherein:
a) the default page model comprises a printable area element and margin elements, the margin elements comprising a top margin element located along a top edge of the default page model, a bottom margin element located along a bottom edge of the default page model, a left margin element located along a left edge of the default page model, and a right margin element located along a right edge of the default page mode; and
b) the printable area element comprising area on the default page model not allocated to at least one of the margin elements.

11. The method of claim 1, wherein the request to print at least one selected medical image of the one or more medical images comprises a paper size selection, and the retrieving a default page model comprises retrieving a default page model based on the paper size selection.

12. The method of claim 1, wherein the determining an image area based on the printable area element of the default page model and the request comprises determining the image area width based on a width of the printable area element of the default page model.

13. The method of claim 1, wherein:
a) the request comprises a selected image layout, the selected image layout comprising a number of image rows per page and a number of image columns per page; and
b) the creating a single page model based on the request comprises:
i. determining an image element height based on the image area height divided by the number of image rows per page;
ii. determining an image element width based on the image area width divided by the number of image columns per page; and
iii. adding at least one image element to the single page model based on the selected image layout, the at least one image element comprising area allocated to the image area, each of the image elements having the image element height and the image element weight.

14. The method of claim 1, wherein:
a) the request comprises at least one header section to be included; and
b) the creating a single page model based on the request comprises:
i. determining a header section width based on the width of the printable area element divided by a number of the at least one header section to be included; and
ii. adding at least one header section element to the single page model based on the at least one header section to be included, the at least one header section element comprising area allocated to the printable area element and not allocated to the image area, each of the header section elements having the header section width.

15. The method of claim 1, wherein:
a) the request comprises at least one footer section to be included; and
b) the creating a single page model based on the request comprises:
i. determining a footer section width based on the width of the printable area element divided by a number of the at least one footer section to be included; and
ii. adding at least one footer section element to the single page model based on the at least one footer section to be included, the at least one footer section element comprising area allocated to the printable area element and not allocated to the image area, each of the footer section elements having the footer section width.

16. The method of claim 1, the creating a base model based on the single page model and the request comprises:
a) determining a number of pages required to print the at least one selected medical image based on the selected image layout; and
b) duplicating the single page model for the number of pages required to print the at least one selected medical image.

17. A system for printing medical images, the system comprising:
a) a server in data communication with a client device; and
b) the client device comprising:
i. communication subsystem for receiving one or more medical images from the server;
ii. a user interface device for displaying the one or more medical images in an Internet browser and receiving a request to print at least one selected medical image of the one or more medical images;
iii. a memory for storing a plurality of instructions; and
iv. a processor operatively coupled to the memory, the user interface device, and the communication subsystem, the processor configured for:
a. in response to receiving the request, generating a base model comprising at least one page required to print the at least one selected medical image, each page of the base model having identical image elements as any other page of the base model;

b. generating a printable model by, for each of the at least one selected medical image, rendering that selected image to an image element of a page of the base model; and c. transferring the printable model to a model printable by the Internet browser;

wherein:

generating a base model comprises:

a) retrieving a default page model to print at least one selected medical image of the one or more medical images, the default page model comprising a printable area element;

b) creating a single page model based on the request by determining an image area based on the printable area element of the default page model and the request, the image area comprising an image area width and an image area height, the single page model comprising the default page model and at least one of an image element, a header section element, and a footer section element, each of the at least one of the image element, the header section element, and the footer section element comprising area allocated to the printable area element; and c) creating a base model based on the single page model and the request;

creating a single page model based on the request comprises; and determining an image area based on the printable area element of the default page model and the request comprises determining the image area height by:

a) creating a test model comprising the default page model, a header element and a footer element, the header element comprising area allocated to the printable area element and located along a top edge of the printable area element, the header element having an associated height based on the request, the footer element comprising area allocated to the printable area element and located along a bottom edge of the printable area element, the footer element having an associated height based on the request;

b) rendering the test model to a document object model of the Internet browser;

c) measuring, from the document object model having the test model, a shortest distance between the header element and the footer element; and d) determining the image area height based on the shortest distance between the header element and the footer element.

18. The system of claim 17, wherein:

a) the at least one selected medical image comprises an ordered set of one or more selected medical images, the ordered set of one or more selected medical images comprising a first selected medical image and one or more subsequent selected medical images, each of the subsequent selected medical images having a corresponding previous selected medical image; and b) the generating a printable model by, for each of the at least one selected medical image, rendering that selected image to an image element of a page of the base model comprises for each subsequent selected medical image, rendering the subsequent selected medical image after the corresponding previous selected medical image has been rendered.

\* \* \* \* \*